(12) United States Patent
Cha et al.

(10) Patent No.: US 10,690,619 B2
(45) Date of Patent: Jun. 23, 2020

(54) APPARATUS AND METHOD FOR MEASURING CONCENTRATION OF AN ANALYTE IN WHOLE BLOOD SAMPLES

(71) Applicant: I-SENS, INC., Seoul (KR)

(72) Inventors: Geun Sig Cha, Seoul (KR); Hakhyun Nam, Seoul (KR); Seok-Won Lee, Seongnam-si (KR); Sung Hyuk Choi, Gwacheon-si (KR); Youngjea Kang, Seoul (KR); Myeongho Lee, Seoul (KR); Ho Dong Park, Wonju-si (KR); Sung Pil Cho, Wonju-si (KR)

(73) Assignee: I-SENS, INC., Seoul (KR)

( * ) Notice: Subject to any disclaimer, the term of this patent is extended or adjusted under 35 U.S.C. 154(b) by 1002 days.

(21) Appl. No.: 14/564,002

(22) Filed: Dec. 8, 2014

(65) Prior Publication Data

US 2016/0077037 A1 Mar. 17, 2016

(30) Foreign Application Priority Data

Sep. 17, 2014 (KR) .......................... 10-2014-0123816

(51) Int. Cl.
*G01N 27/327* (2006.01)
*G01N 33/49* (2006.01)
(Continued)

(52) U.S. Cl.
CPC ..... *G01N 27/3274* (2013.01); *G01N 27/3272* (2013.01); *G01N 33/48707* (2013.01);
(Continued)

(58) Field of Classification Search
CPC ............... G01N 27/3274; G01N 33/49; G01N 33/48707; G01N 27/3272; G01N 33/26;
(Continued)

(56) References Cited

U.S. PATENT DOCUMENTS 3,648,160 A 3/1972 Beaver
3,922,598 A 11/1975 Steuer et al.
(Continued)

FOREIGN PATENT DOCUMENTS

CN 102128862 A 7/2011
CN 102132150 A 7/2011
(Continued)

OTHER PUBLICATIONS

Extended European Search Report dated Feb. 10, 2016, which issued in European Application No. 14192132.0.

*Primary Examiner* — Michael Y Sun
(74) *Attorney, Agent, or Firm* — Morgan, Lewis & Bockius LLP

(57) ABSTRACT

A method for measuring a concentration of an analyte in a bio-sample using an electrochemical bio-sensor according to an exemplary embodiment of the present invention is characterized by a step of obtaining predetermined features from induced currents obtained by applying a DC voltage according to chronoamperometry in which, after a whole blood sample is injected to the electrochemical bio-sensor, a concentration of an analyte is obtained from an induced current obtained by applying a DC voltage for a certain time and from all induced currents obtained by further applying several step-ladder perturbation potentials for a short time subsequent to the DC voltage for the certain time, and is also characterized by minimization of a measurement error caused by a hindering material by forming a calibration equation by combining the at least one feature in a function and optimizing various conditions of the bio-sample through DeletedTextsmultivariable analysis. With this configuration, a perturbation potential application method added to a conventional measurement method can maintain a bio-sensor and a measuring apparatus already used, a line used in the measuring apparatus, and calibration of amperometry (Continued)

as they are, improve accuracy in measurement by effectively minimizing a matrix interference effect of a background material in a bio-sample, particularly an inaccuracy caused by a change in hematocrit, and also remarkably improve accuracy in measurement by simply upgrading a measurement program of a conventional measuring apparatus.

11 Claims, 16 Drawing Sheets

(51) Int. Cl.
G01N 33/487 (2006.01)
C12Q 1/00 (2006.01)
G01N 33/543 (2006.01)
A61B 5/1468 (2006.01)
G01N 33/53 (2006.01)
B01L 3/00 (2006.01)
A61B 5/1495 (2006.01)
A61B 5/145 (2006.01)
G01N 27/49 (2006.01)
G01N 33/26 (2006.01)
G01N 33/52 (2006.01)
G01N 27/48 (2006.01)
G01N 27/42 (2006.01)

(52) U.S. Cl.
CPC ............ *G01N 33/49* (2013.01); *A61B 5/1468* (2013.01); *A61B 5/1495* (2013.01); *A61B 5/14532* (2013.01); *A61B 2562/0295* (2013.01); *B01L 3/5023* (2013.01); *B01L 2200/16* (2013.01); *B01L 2300/0645* (2013.01); *B01L 2300/0825* (2013.01); *C12Q 1/001* (2013.01); *C12Q 1/002* (2013.01); *G01N 27/3271* (2013.01); *G01N 27/3273* (2013.01); *G01N 27/3277* (2013.01); *G01N 27/42* (2013.01); *G01N 27/48* (2013.01); *G01N 27/49* (2013.01); *G01N 33/26* (2013.01); *G01N 33/4875* (2013.01); *G01N 33/48771* (2013.01); *G01N 33/52* (2013.01); *G01N 33/5302* (2013.01); *G01N 33/5438* (2013.01)

(58) Field of Classification Search
CPC ........ G01N 33/52; G01N 27/48; G01N 27/42; G01N 27/49; G01N 33/48771; G01N 33/4875; G01N 27/3277; G01N 33/5438; G01N 33/5302; G01N 27/3271; G01N 27/3273; G01N 15/06; G01N 27/26; G01N 33/48; G01N 33/50; B01L 2200/16; B01L 3/5023; B01L 2300/0825; B01L 2300/0645; C12Q 1/002; C12Q 1/001; A61B 5/1495; A61B 5/14532; A61B 2562/0295; A61B 5/1468
See application file for complete search history.

(56) References Cited

U.S. PATENT DOCUMENTS

| | | | |
|---|---|---|---|
| 4,068,169 A | 1/1978 | Angel et al. | |
| 4,547,735 A | 10/1985 | Kiesewetter et al. | |
| 4,699,887 A | 10/1987 | Abbott et al. | |
| 4,897,162 A * | 1/1990 | Lewandowski | G01N 27/3271 204/402 |
| 5,264,103 A | 11/1993 | Yoshioka et al. | |
| 5,708,247 A | 1/1998 | McAleer et al. | |
| 6,287,451 B1 | 9/2001 | Winarta et al. | |
| 7,258,769 B2 | 8/2007 | Cui et al. | |
| 7,338,639 B2 | 3/2008 | Burke et al. | |
| 7,390,667 B2 | 6/2008 | Burke et al. | |
| 7,407,811 B2 | 8/2008 | Burke et al. | |
| 2003/0146110 A1* | 8/2003 | Karinka | C12Q 1/002 205/777.5 |
| 2004/0108223 A1* | 6/2004 | Jansson | G01N 27/42 205/775 |
| 2007/0062822 A1 | 3/2007 | Fujiwara et al. | |
| 2008/0000780 A1* | 1/2008 | Tonks | G01N 27/3274 205/792 |
| 2010/0243476 A1 | 9/2010 | Fujiwara et al. | |
| 2010/0276303 A1 | 11/2010 | Fujiwara et al. | |
| 2011/0073492 A1* | 3/2011 | Reich | G01N 27/3277 205/777.5 |
| 2011/0125447 A1 | 5/2011 | Shah et al. | |
| 2011/0139634 A1 | 6/2011 | Chou et al. | |
| 2011/0155588 A1* | 6/2011 | Lica | G01N 27/3273 205/782 |
| 2012/0132540 A1* | 5/2012 | Wang | A61B 5/14532 205/775 |
| 2013/0305081 A1* | 11/2013 | Agnihotram | G06F 11/0793 714/2 |
| 2014/0135605 A1 | 5/2014 | Gottlieb et al. | |

FOREIGN PATENT DOCUMENTS

| | | |
|---|---|---|
| CN | 102667475 A | 9/2012 |
| JP | 2000-180399 A | 6/2000 |
| JP | 2005-515413 A | 5/2005 |
| JP | 2010-101839 A | 5/2010 |
| JP | 2011-506964 A | 3/2011 |
| JP | 2012-247433 A | 12/2012 |
| JP | 2013-516598 A | 5/2013 |
| JP | 05280244 B2 | 9/2013 |
| JP | WO 2013-073074 A1 | 4/2015 |
| KR | 10-2013-0131117 A | 12/2013 |
| KR | 10-2013-0135605 A | 12/2013 |
| KR | 10-2014-0015387 A | 2/2014 |
| WO | WO-95/02357 A1 | 1/1995 |
| WO | WO-2007/079015 A2 | 7/2007 |
| WO | WO-2013/183215 A1 | 12/2013 |
| WO | WO-2014/078409 A1 | 5/2014 |

* cited by examiner

APPARATUS AND METHOD FOR MEASURING CONCENTRATION OF AN ANALYTE IN WHOLE BLOOD SAMPLES

CROSS-REFERENCE TO RELATED APPLICATION

This application claims priority to and the benefit of Korean Patent Application No. 10-2014-0123816 filed in the Korean Intellectual Property Office on Sep. 17, 2014, the entire contents of which are incorporated herein by reference.

BACKGROUND OF THE INVENTION

(a) Field of the Invention

The present invention relates to an apparatus and a method for measuring a concentration of an analyte in a bio-sample, and more particularly, to an apparatus and a method for measuring a concentration of an analyte in a bio-sample by which concentrations of blood samples can be measured with minimum deviation caused by a hindering material by additionally applying a step ladder-type perturbation potential for a short time and optimizing a function formed of features obtained from induced currents in regions, to which a constant voltage and the perturbation potential are applied, as a calibration equation for multivariable regression analysis with respect to the blood samples under various conditions if there is wide deviation in measurement results due to various hindering materials of blood, particularly, hematocrit when concentrations of the blood samples are measured by chronoamperometry.

(b) Description of the Related Art

It is important to measure a concentration of a clinically important material for the sake of diagnosis and health care. Particularly, measurement of a concentration of a metabolite (analyte) such as glucose, ketone, creatine, lactate, neutral fat, pyruvate, alcohol, bilirubin, NAD(P)H, and uric acid from fluid in vivo such as blood becomes the key to diagnosis of a disease and care of symptoms of a disease.

As a method for accurately, rapidly, and economically measuring a concentration of a clinically significant material from fluid in vivo, a method using an electrochemical bio-sensor has been widely used.

In such an electrochemical bio-sensor (sometimes referred to as a "strip"), a pair of electrodes (a working electrode and an counter electrode) in which a sample cell having a capillary tube structure is coated with a reagent including an enzyme, an electron transfer mediator, and various stabilizers and dispersants are disposed.

If the sample cell of the electrochemical bio-sensor is filled with blood of a user and then installed in a portable measuring apparatus, a constant voltage is applied to the working electrode and a current obtained from the working electrode is measured. A concentration of an analyte calculated according to a programmed algorithm is displayed on a screen of the portable measuring apparatus within several seconds to several minutes.

Measurement and monitoring of a metabolite, i.e. an analyte, using such an electrochemical bio-sensor is fast, convenient, and inexpensive, and thus has been widely used all over the world.

However, users and health management organizations in many countries have demanded an electrochemical bio-sensor with accuracy as well as convenience, and such a demand has been specified as international standards such as DeletedTextsISO 15197:2013.

Hematocrit is one important factor among factors hindering accuracy of an electrochemical bio-sensor that measures a concentration in blood. This is because movement and diffusion speed of an oxidation/reduction reaction material depends on hematocrit of a whole blood sample and greatly affects a measured current signal.

For example, even if blood samples have the same blood glucose concentration, in a blood sample having a higher hematocrit, there is resistance to movement of an oxidation/reduction reaction material. Thus, a measured current signal is decreased. On the contrary, in a blood sample having a lower hematocrit, a measured current signal is increased.

Such an increase or decrease in a current signal causes a measured blood glucose concentration to be lower or higher than it actually is and thus makes the measurement inaccurate. In order to correct such inaccuracy, technologies for improving accuracy by adjusting an electrochemical reaction time to be longer or introducing an additional device into a bio-sensor even if accepting an increase in cost of measurement have been suggested.

A method of removing red blood cells in advance with a filter and then measuring an analyte in an effort to minimize a deviation caused by hematocrit has been suggested (U.S. Pat. Nos. 5,708,247 and 5,951,836). Such a method may be effective, but needs a sensor to be manufactured by adding a filter to a strip, and thus a manufacturing process may be complicated and costs of products may be increased.

Red blood cells hinder diffusion and movement of a material in a blood sample and thus changes resistance of blood. Thus, a method of reducing a deviation caused by hematocrit using a net structure has been suggested (U.S. Pat. No. 5,628,890).

Further, a method in which red blood cells are hemolyzed with a reagent and hemoglobin flowing out to blood plasma subsidiarily controls an increase/decrease in a current signal caused by a change in hematocrit has been suggested (U.S. Pat. No. 7,641,785). However, the above-described methods are limited in effect in a wide range of hematocrit.

Recently, a method of correcting a deviation caused by hematocrit by electrochemically obtaining an additional signal has been suggested. For example, there is a method in which an AC voltage is applied and impedance of a blood sample is measured, and after a hematocrit value is measured, a measurement value of an analyte is corrected using the measured hematocrit value (U.S. Pat. No. 7,390,667 and U.S. Patent Laid-open Publication Nos. 2004-0079652, 2005-0164328, 2011-0139634, and 2012-0111739).

However, such methods require application of a simple DC voltage to a measuring apparatus to measure impedance and also require an additional circuit for measuring AC and impedance in addition to a current measuring circuit, and a bio-sensor is provided with an additional electrode for measuring conductivity or impedance. Therefore, such methods may increase complexity and cost of the overall measuring system (U.S. Pat. No. 7,597,793 and U.S. Patent Laid-open Publication No. 2011-0139634).

Further, many Patent Documents have suggested methods of obtaining a plurality of induced current values while mixing and applying a plurality of square wave voltages different from each other in level at various time intervals without using an AC voltage, and compensating hematocrit based on the obtained induced current values (U.S. Pat. Nos. 6,475,372 and 8,460,537, U.S. Patent Laid-open Publication No. 2009-0026094, European Patent Laid-open Publication No. 2,746,759, and WO2013/164632).

These methods have a merit in that they can be applied even without replacing a conventional bio-sensor or measuring apparatus. However, in these methods, not only may a current caused by an induced electrochemical reaction among a material to be measured, an enzyme, and an electron transfer mediator be generated, but also a current (background current) caused by an uncontrollable electrochemical reaction between oxidation/reduction reaction materials remaining at an electrical double layer on an electrode surface when an applied voltage is sharply changed may be generated.

Therefore, as for bio-sensors produced under mass production, a surface status of an electrode or solubility of a reagent and homogeneity of a reaction in each strip sensor cannot be exactly the same, and thus it is difficult to regulate precision of a background current generated when an applied voltage is sharply changed within a statistical error range. Further, it is impossible to precisely regulate a charging current generated when an applied voltage is sharply changed to be equivalent in each bio-sensor electrode. Therefore, precision in correction may be decreased.

The present inventors found that cyclic voltammetry with periodicity can be effective in reducing a deviation with respect to hematocrit, and applied the cyclic voltammetry together with chronoamperometry (Korean Patent Laid-open Publication No. 2013-0131117).

As compared with other methods using various mixed square wave voltages to correct hematocrit, this method can reduce an effect of an unstable charging current caused by a sharp change in voltage, and while the voltages are scanned, concentrations of oxidation/reduction reaction materials present within an electrical double layer on an electrode surface are changed with an appropriate gradient of voltage compared with a change in voltage. Therefore, a background current to be generated is regulated within a specific range, and thus it is possible to improve an overall correction effect.

However, in this method, hematocrit is separately estimated using currents obtained by the cyclic voltammetry, and then the estimated hematocrit is applied to an equation for a concentration so as to correct an effect of hematocrit. Thus, the overall correction effect largely depends on accuracy of the estimated hematocrit.

Further, this method may need a complicated measuring circuit as compared with a case where only chronoamperometry with a constant square wave voltage is used in order to stably implement the cyclic voltammetry and measure induced currents corresponding thereto.

A method of measuring a concentration of blood in which hematocrit is corrected by acyclically applying voltages on forward and reverse scan using acyclic voltammetry in an electrochemical bio-sensor has been suggested (U.S. Pat. No. 8,287,717).

Likewise, in this method, hematocrit needs to be obtained by appropriately mixing induced currents formed of voltage functions which can be obtained by applying the acyclic voltammetry, the hematocrit obtained by an additional equation needs to be applied to the equation for a concentration of blood to remove a matrix effect, and an additional circuit capable of responding to a rapid scan in a wide voltage range is needed.

In addition to the above-described methods, many efforts to minimize or remove an effect of hematocrit can be found. However, most of these methods need a new strip structure or need to use a measuring apparatus including an additional circuit structure, or cannot use conventional strips and measuring apparatuses.

The above information disclosed in this Background section is only for enhancement of understanding of the background of the invention and therefore it may include information that does not form the prior art that is already known in this country to a person of ordinary skill in the art.

SUMMARY OF THE INVENTION

The present invention has been made in an effort to provide a method and an apparatus for measuring a concentration of an analyte in a bio-sample capable of reducing a measurement error depending on hematocrit by using hardware of a conventional strip and a conventional measuring apparatus, and simply upgrading firmware of the measuring apparatus.

The present invention has also been made in an effort to provide a method and an apparatus for measuring a concentration of an analyte in a bio-sample capable of effectively and economically removing or minimizing hindrance of materials in blood by applying a constant voltage as a main voltage and using a step ladder-type voltage to be consecutively applied as a perturbation potential.

The present invention has also been made in an effort to provide a method and an apparatus for measuring a concentration of an analyte in a bio-sample capable of remarkably reducing an effect of hematocrit while using approximately the same calibration method used for a conventional product by utilizing various information obtained by consecutively applying a step ladder-type voltage to chronoamperometry for a short time while using the same chronoamperometry as is used for a conventional electrochemical bio-sensor and a conventional measuring apparatus.

An exemplary embodiment of the present invention provides a method for measuring a concentration of an analyte in a bio-sample using an electrochemical bio-sensor, the method including, after a liquid bio-sample is injected to a sample cell in which an enzyme capable of catalyzing an oxidation/reduction reaction of the analyte and an electron transfer mediator are fixed and a working electrode and an counter electrode are provided, a step of obtaining a first induced current by applying a constant DC voltage to the working electrode to start the oxidation/reduction reaction of the analyte and proceed with an electron transfer reaction, a step of obtaining a second induced current by applying a $\Lambda$-step ladder-type perturbation potential after applying the constant DC voltage, a step of calculating a predetermined feature from two or more characteristic points from the first induced current or the second induced current, and a step of calculating a concentration of the analyte using a calibration equation formed of at least one feature function decreased in effect of hindering materials in the bio-sample.

Another exemplary embodiment of the present invention provides an apparatus for measuring a concentration of an analyte in a bio-sample using an electrochemical bio-sensor, the apparatus including:

a connector to which a sample cell in which an oxidation/reduction enzyme capable of catalyzing an oxidation/reduction reaction of the analyte and an electron transfer mediator are fixed and a working electrode and an counter electrode are provided is inserted;

a digital-to-analog converter circuit configured to apply a constant DC voltage to start the oxidation/reduction reaction of the analyte, proceed with an electron transfer reaction, and apply a Λ-step ladder-type perturbation potential for fluctuating a potential of the sample cell after applying the constant DC voltage; and a microcontroller configured to control the digital-to-analog converter circuit and directly obtain a concentration value of the analyte from a calibration equation using the Λ-step ladder-type perturbation potential.

In the method and the apparatus for measuring a concentration of an analyte in a bio-sample according to an exemplary embodiment of the present invention, the first or second induced current different from each other in characteristics with respect to a constant voltage and an applied voltage formed of a Λ (lambda)-step ladder-type perturbation pulse (or perturbation potential) are modified to a predetermined feature, and a calibration equation is obtained by an appropriate statistical mathematical method. Therefore, it is possible to measure a concentration of the analyte material by removing or minimizing a matrix effect of background materials of the bio-sample.

Among hindering factors which can be effectively reduced by the method and the apparatus for measuring a concentration of an analyte in a bio-sample according to an exemplary embodiment of the present invention, a representative example for a blood sample is hematocrit. It is not necessary to improve a structure of an electrochemical bio-sensor, i.e. a strip, or a reagent, and a structure of a measuring apparatus can also use a conventional circuit for measuring a current value by applying a constant voltage.

Further, the method and the apparatus for measuring a concentration of an analyte in a bio-sample according to an exemplary embodiment of the present invention do not modify a chronoamperometric section typically used in the conventional market and obtain a correction signal from a range of a perturbation potential to be subsequently applied. Therefore, it is possible to minimize a deviation with respect to hematocrit while maintaining conventional measuring performance and characteristics.

Also, the method and the apparatus for measuring a concentration of an analyte in a bio-sample according to an exemplary embodiment of the present invention are capable of determining a concentration of an analyte using a calibration equation obtained through multivariable regression analysis by comparing a function formed of features extracted from an induced current so as to be minimized in deviation with respect to hematocrit with the standard test results. Thus, an additional process of obtaining hematocrit is not needed, and fluctuation in precision which may occur during a process of obtaining two different measurement values can be minimized.

The apparatus for measuring a concentration of an analyte in a bio-sample according to an exemplary embodiment of the present invention upgrades and inputs a program programmed using the calibration equation determined according to the method for measuring a concentration of an analyte in a bio-sample according to an exemplary embodiment of the present invention. Thus, it is possible to obtain a concentration of an analyte minimized in effect of hematocrit using a conventional strip and hardware as they are.

Further, the method for measuring a concentration of an analyte in a bio-sample according to an exemplary embodiment of the present invention is capable of more accurately determining a concentration of an analyte through a more economical and efficient process as compared with a process in which hematocrit is obtained and then separately applied to a calibration equation.

DETAILED DESCRIPTION OF THE EMBODIMENTS

Figure 1:
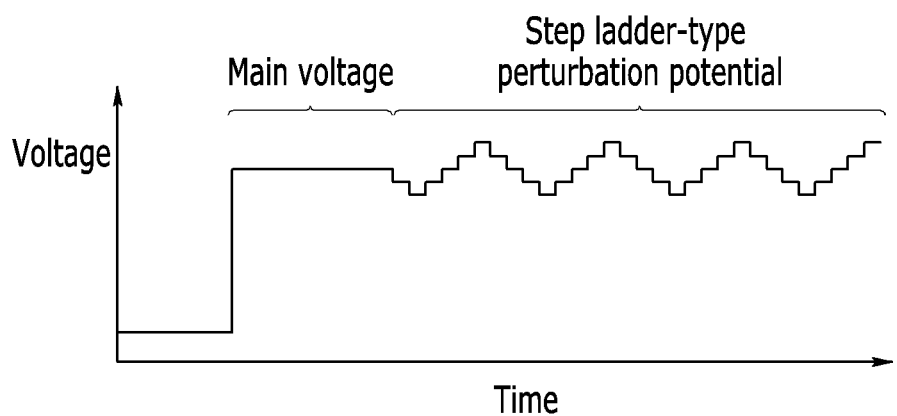
FIG. 1 is a graph illustrating a Λ-step ladder-type perturbation potential used in a method for measuring a concentration of an analyte in a bio-sample according to an exemplary embodiment of the present invention.

Hereinafter, a method and an apparatus for measuring a concentration of an analyte in a bio-sample according to exemplary embodiments of the present invention will be explained in detail with reference to the accompanying drawings.

In the present specification, it will be explained that correcting a measurement error generated due to hematocrit during measurement of blood glucose is desirable in an exemplary embodiment. However, in the same manner as a glucose test, by introducing a specific enzyme, it is possible to correct concentration measurement values of various metabolites such as organic materials including β-hydroxybutyric acid, cholesterol, triglyceride, lactate, pyruvate, alcohol, bilirubin, uric acid, phenylketonuria, creatine, creatinine, glucose-6-phosphate dehydrogenase, and NAD(P)H, or inorganic materials.

Therefore, the present invention can be applied to quantification of various metabolites by varying a kind of an enzyme included in a sample layer composition.

For example, quantification of glucose, glutamate, cholesterol, lactate, ascorbic acid, alcohol, and bilirubin can be carried out using a glucose oxidase (GOx), a glucose dehydrogenase (GDH), a glutamate oxidase, a glutamate dehydrogenase, a cholesterol oxidase, a cholesterol esterase, a lactate oxidase, an ascorbic acid oxidase, an alcohol oxidase, an alcohol dehydrogenase, a bilirubin oxidase, and the like.

An electron transfer mediator which can be used together with the above-described enzymes may be one of ferrocene, ruthenium hexamine(III) chloride, potassium ferricyanide, 1,10-phenanthroline-5,6-dione, and bipyridine, or an osmium complex including phenanthroline as a ligand, 2,6-dimethyl-1,4-benzoquinone, 2,5-dichloro-1,4-benzoquinone, 3,7-diamino-5-phenothiaziniumthionine, 1-methoxy-5-methylphenazinium methylsulfate, methylene blue, and toluidine blue, but may not be limited to these compounds and may include organic and inorganic electron transfer mediators capable of transferring an electron together with an enzyme capable of catalyzing an oxidation/reduction reaction of a metabolite.

As a portable measuring apparatus according to an exemplary embodiment of the present invention, a vis-a-vis electrochemical bio-sensor in which a working electrode and an counter electrode are provided on different planes so as to face each other and a reagent composition including an enzyme and an electron transfer mediator depending on a material is coated on the working electrode may be employed.

Further, as a portable measuring apparatus according to an exemplary embodiment of the present invention, a planar electrochemical bio-sensor in which a working electrode and an counter electrode are provided on the same plane and a reagent composition including an enzyme and an electron transfer mediator depending on a material is coated on the working electrode may be employed.

Hereinafter, a method and an apparatus for measuring a concentration of an analyte in a bio-sample according to exemplary embodiments of the present invention will be explained in detail with reference to FIG. 1 to FIG. 5.

Figure 2:
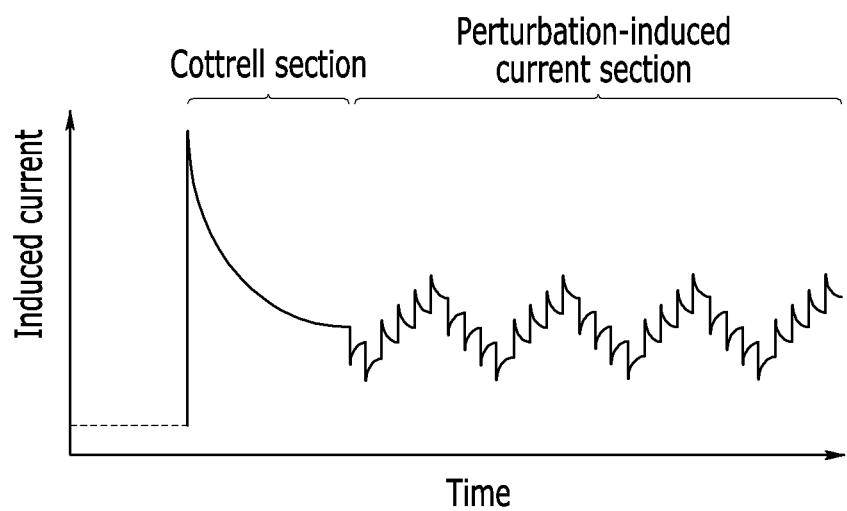
FIG. 2 is a graph illustrating an induced current obtained in correspondence with the voltage applied as illustrated in FIG. 1.
Figure 3:
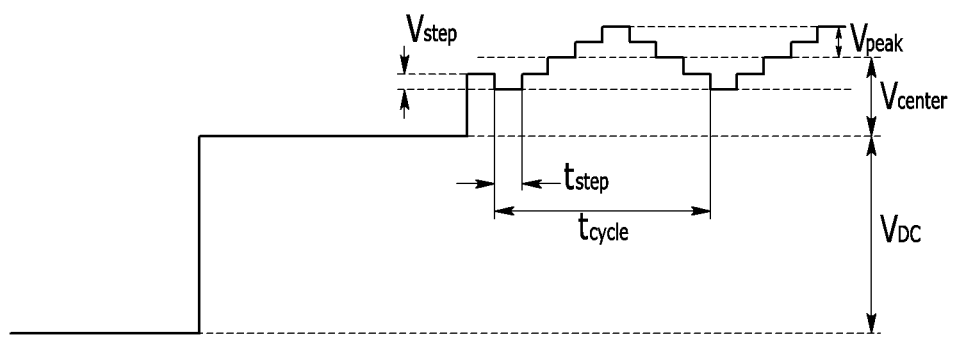
FIG. 3 is a graph provided to explain a structure of a Λ-step ladder-type perturbation potential used in a method for measuring a concentration of an analyte in a bio-sample according to an exemplary embodiment of the present invention.
Figure 4:
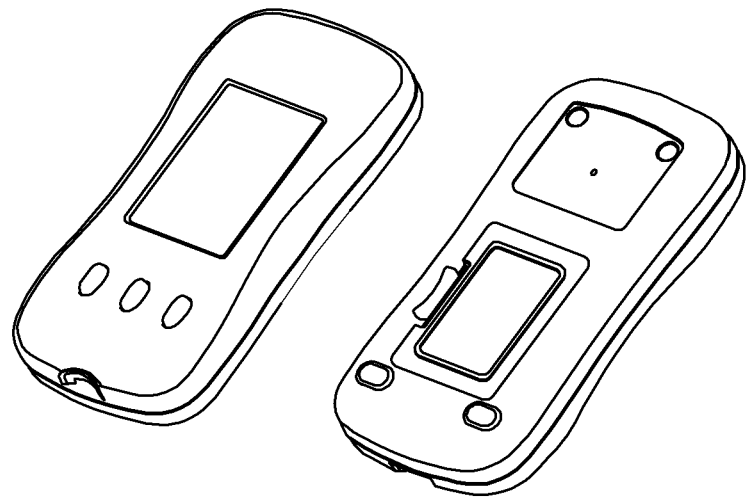
FIG. 4 provides front and rear perspective views of a measuring apparatus in which a calibration equation by means of a method for measuring a concentration of an analyte in a bio-sample according to an exemplary embodiment of the present invention is stored.
Figure 5:
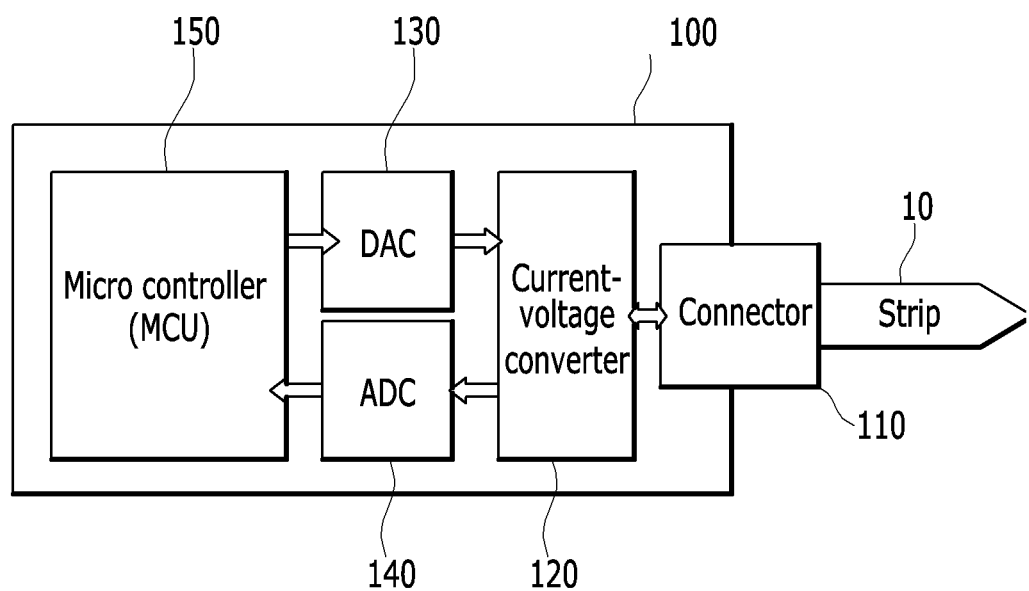
FIG. 5 is a block diagram illustrating a circuit of the measuring apparatus for measuring a concentration of an analyte in a bio-sample as illustrated in FIG. 4.

FIG. 1 and FIG. 2 are graphs respectively illustrating a Λ-step ladder-type perturbation potential used in a method for measuring a concentration of an analyte in a bio-sample and an induced current obtained in correspondence with the voltage according to an exemplary embodiment of the present invention, FIG. 3 is a graph provided to explain a structure of a Λ-step ladder-type perturbation potential used in a method for measuring a concentration of an analyte in a bio-sample according to an exemplary embodiment of the present invention, FIG. 4 provides front and rear perspective views of a measuring apparatus in which a calibration equation by means of a method for measuring a concentration of an analyte in a bio-sample according to an exemplary embodiment of the present invention is stored, and FIG. 5 is a block diagram illustrating a circuit of the measuring apparatus for measuring a concentration of an analyte in a bio-sample as illustrated in FIG. 4.

As illustrated in FIG. 1, in a method for measuring a concentration of an analyte in a bio-sample according to an exemplary embodiment of the present invention, a step ladder-type perturbation potential is applied consecutively after a constant voltage ($V_{DC}$) is applied. Accordingly, an induced current is measured.

As illustrated in FIG. 3, a perturbation potential used in the method for measuring a concentration of an analyte in a bio-sample according to the exemplary embodiment of the present invention is formed of a step ladder-type wave, the perturbation potential is characterized by a height ($V_{step}$) of each step, an application time ($t_{step}$) for each step, a difference ($V_{center}$) between a middle voltage and a constant voltage in the entire range of variations, a difference ($V_{peak}$) between the middle voltage and a peak voltage, and a time difference ($t_{cycle}$) between a peak voltage of the entire step ladder-type wave and the peak voltage of the adjacent next step ladder-type wave, and has a range as listed in the following Table 1.

Table 1 listing a range of a step ladder-type wave is just one exemplary embodiment of the present invention, and can be modified and changed in various ways depending on application.

TABLE 1

|  | Minimum value | Appropriate value | Maximum value |
|---|---|---|---|
| $V_{step}$ | 0.5 mV | 1-10 mV | 20 mV |
| $t_{step}$ | 0.001 s | 0.01-0.05 s | 0.1 s |
| $V_{DC}$ | 50 mV | 150-300 mV | 800 mV |
| $V_{center}$ | −150 mV | −100-100 mV | 150 mV |
| $V_{peak}$ | 5 mV | 12-60 mV | 150 mV |
| $t_{cycle}$ | 0.01 s | 0.05-0.2 s | 1 s |

In the method for measuring a concentration of an analyte in a bio-sample according to the exemplary embodiment of the present invention, current values used for determining a concentration of the analyte are points which can be obtained from one step or a plurality of steps of a first or second induced current.

As illustrated in FIG. 4, a concentration measuring apparatus 100 for measuring a concentration of an analyte in a bio-sample according to an exemplary embodiment of the present invention is capable of obtaining an additional signal for correction within several seconds and preferably within 0.1 to 1 second by applying a perturbation potential that changes a potential while maintaining a pair of a working electrode and an counter electrode of a conventional electrochemical bio-sensor, i.e., a strip 10.

As illustrated in FIG. 5, the concentration measuring apparatus 100 for measuring a concentration of an analyte in a bio-sample according to the exemplary embodiment of the present invention is configured such that if the electrochemical bio-sensor 10 is provided at a connector 110, the connector 110 is electrically connected to a current-voltage converter 120, and a microcontroller (MCU) 150 can apply a perturbation potential to the working electrode of the strip 10 without an additional perturbation potential circuit through a digital-to-analog converter (DAC) circuit 130 provided at the concentration measuring apparatus 100 to apply a constant voltage according to the conventional chronoamperometry.

To do so, firmware of the concentration measuring apparatus 100 for measuring a concentration of an analyte in a bio-sample according to the exemplary embodiment of the present invention stores a predetermined constant which can generate a perturbation potential in a memory of the measuring apparatus 100, records a predetermined constant at a register of the DAC circuit 130 when a constant voltage is applied, and increases/decreases the constant stored in the memory at a predetermined time interval and records the constant at the register of the DAC circuit 130 when the perturbation potential is applied.

The microcontroller 150 applies an adequate voltage between the two electrodes of the strip depending on a constant recorded at the register of the DAC circuit 130.

The first or second induced current measured by the strip 10 can be directly measured by an analog-to-digital converter (ADC) circuit 140 through the connector 110 and the current-voltage converter 120.

When the perturbation potential is formed of a step form wave as illustrated in FIG. 3, a circuit can be simplified as compared with the other methods using AC or a linear scanning method, and it is possible to reduce generation of a charging current which may be a hindrance to analysis when pulses of various voltages are used.

As illustrated in FIG. 1, if a step ladder-type wave is applied at a regular interval at a constant amplitude right after a constant voltage is applied, a distribution of concentrations of components to be oxidized/reduced in a diffusion layer near the electrode fluctuates.

Such fluctuation or perturbation causes an important change in characteristics of an induced current, and this change can be an important means capable of removing or minimizing an effect of hematocrit with current values obtained from one step or a plurality of steps constituting a step ladder-type wave.

Herein, an induced current is expressed as a first induced current or a second induced current in order to show that they are different from each other due to a change in characteristics of the induced current caused by fluctuation or perturbation.

An application type of a step ladder-type perturbation potential having periodicity and additionally applied for a short time in order to remove an effect of hematocrit from a calibration equation after a constant voltage is applied will be referred to as a "Λ-step ladder-type perturbation potential" or simply as a "step ladder potential".

The above-described currents that are different from each other in characteristics refer to currents which can be used as variables for effectively separating or correcting an effect of hematocrit since they differently depend on blood glucose and hematocrit (hindering material).

For example, if two or more voltage pulses are applied at an appropriate time interval and first and second induced currents are measured from each pulse, and values of the first and second induced currents are determined depending on blood glucose and hematocrit and thus can be expressed by the following functions $g_1$ and $g_2$ of blood glucose and hematocrit.

If the blood glucose and the hematocrit contribute to the currents in the same manner in the current functions $g_1$ and $g_2$ and a linear formula of constants in the form of $i_1 = ki_2$ is established, it will be said that the current have the same characteristics, and if not, it will be said that the currents have different characteristics.

As for the currents having the same characteristics, it is impossible to accurately calculate an effect of hematocrit or it is difficult to correct an effect of hematocrit due to linear dependency among variables during regression analysis.

However, as for an induced current which can be obtained by applying a step ladder-type perturbation potential, a level of fluctuation in a sample is continuously changed near an electrical double layer when each step moves up or down for a short time and an electron transfer speed and an effect of a charging current are changed accordingly. Thus, it may be different from the current obtained according to chronoamperometry in characteristics.

As such, elements useful for forming a calibration equation used for the method for measuring a concentration of an analyte in a bio-sample according to an exemplary embodiment of the present invention due to a great difference in characteristics between first and second induced currents corresponding to a constant voltage and a perturbation potential will be referred to as characteristic points, and non-modified current values of the characteristic points or values appropriately modified to be variables suitable for a calibration equation will be referred to as features.

In an electrochemical bio-sensor, an induced current obtained according to chronoamperometry can be approximated by the Cottrell equation when a reagent of the bio-sensor is mixed with a sample in a sample cell and reaches a uniform liquid state.

$$i(t) = \frac{nFAD^{\frac{1}{2}}C}{\pi t^{\frac{1}{2}}} = k(t)AD^{1/2}C$$

Herein, n denotes the number of electrons transferred per molecule of a material (for example, an electron transfer mediator) to be oxidized/reduced in an electrode, F denotes the Faraday constant, A denotes an electrode area, D denotes a diffusion coefficient within a sample of the material to be oxidized/reduced, and C denotes a concentration of the material to be oxidized/reduced.

A characteristic point in a chronoamperometric section is a current value at a point which is stably expressed by the Cottrell equation after a constant voltage is applied. In the present electrochemical bio-sensor, it is a time point with a lapse of time of several seconds to several minutes, preferably 1 to 10 seconds, after a constant voltage is applied.

As described above, the second induced current obtained from a step ladder-type perturbation potential is greatly different in characteristics from the first induced current obtained when a constant voltage is applied, and thus it can be used as a variable with high orthogonality in the whole calibration equation.

A method for finding characteristic points from second induced currents corresponding to a section where the perturbation potential is applied and a method for making features with these characteristic points are as follows.

The following method is one of examples and can be modified and changed in various ways depending on a purpose of application.

1) Induced currents near peak and valley voltages of a specific step ladder type wave
2) The curvature of a curved line formed of induced currents of each step of the step ladder type wave
3) A difference between a current value of a peak and a current value of a valley of the step ladder type wave
4) Induced currents in the middle of ups and downs of the step ladder type wave
5) Induced currents at a starting point and an ending point of each step ladder-type cycle
6) An average value of induced currents obtained from the step ladder-type wave
7) Values which can be obtained by expressing the current values obtained from the above features 1 to 6 by the four fundamental arithmetic operations and mathematical functions such as an exponential function, a logarithmic function, and a trigonometric function.

If characteristic points are found from the second induced currents corresponding to the section where the perturbation potential is applied and features are made with current values obtained from these characteristic points and multivariable regression analysis is applied to a linear mixture thereof, it is possible to obtain a calibration equation minimized in effect of hematocrit.

A specific method for making a calibration equation minimized in effect of hematocrit will be explained in detail with reference to the following first to fifth exemplary embodiments.

However, the calibration equation to which multivariable regression analysis is applied by linearly mixing the features may be greatly changed depending on a material of the electrodes used in the electrochemical bio-sensor, arrangement of the electrodes, a shape of a flow path, and a characteristic of a reagent to be used.

The calibration equation used for the method for measuring a concentration of an analyte in a bio-sample according to an exemplary embodiment of the present invention can be applied to a general electrochemical bio-sensor having a sample cell including a pair of a working electrode and an counter electrode. Particularly, if a material to be measured is glucose or a ketone body in blood or a metabolite which can be electrochemically measured, it is useful for analysis of, for example, creatine, lactate, cholesterol, phenylketonuria, glucose-6-phosphate dehydrogenase, and the like.

In order to perform the method of the present invention for measuring a concentration of an analyte in a bio-sample according to an exemplary embodiment of the present invention, a feature function formed using features which can be obtained from first and second induced currents corresponding to a constant voltage and a step ladder-type perturbation potential needs to be optimized by multivariable regression analysis so as to minimize a deviation of hematocrit through experiments using samples under various conditions, and a calibration equation needs to be developed.

Then, the calibration equation is realized by firmware of the measuring apparatus and thus can be used when a blood sample is analyzed.

[First Exemplary Embodiment] Method for Measuring Blood Glucose Using Induced Current Corresponding to Constant Voltage A sample cell of an electrochemical bio-sensor used for a method for measuring a concentration of an analyte in a bio-sample according to a first exemplary embodiment of the present invention is a disposable strip formed of two screen-printed carbon electrodes, and the electrodes are coated with a glucose dehydrogenase and an electron transfer mediator (thionine, ruthenium hexamine chloride).

The measuring apparatus 100 used for the method for measuring a concentration of an analyte in a bio-sample according to the first exemplary embodiment of the present invention is commercially available CareSens N (brand name) as illustrated in FIG. 4.

In the method for measuring a concentration of an analyte in a bio-sample according to the first exemplary embodiment of the present invention, firmware of the measuring apparatus 100 is used as it is to obtain a first induced current corresponding to a constant voltage by applying the constant voltage from the microcontroller 150 to the working electrode through the digital-to-analog converter circuit 130, and a blood glucose value is calculated.

The experiment was conducted at a temperature of 23° C., and YSI equipment was used as reference equipment.

In order to check a deviation caused by hematocrit, blood experiments can be conducted as follows.

Blood collected from venous blood is divided into red blood cells and plasma through centrifugation, and the red blood cells and the plasma are mixed again at an appropriate ratio so as to obtain a desired hematocrit. Then, samples respectively having hematocrit values of 10, 20, 30, 42, 50, 60, and 70% are prepared. A glucose concentration is prepared by adding a glucose solution having a high concentration to each sample.

The blood samples are prepared such that blood glucose values can be approximately 30, 80, 130, 200, 350, 450, and 600 mg/dL with respect to the respective hematocrit values, and an actual blood glucose value of each sample is measured by reference equipment to be determined.

Meanwhile, the measuring apparatus 100 records a first induced current corresponding to a constant voltage according to the conventional chronoamperometry.

A voltage applied at this time is 0 V when being applied between the two carbon electrodes for 3 seconds after inflow of blood, and is 200 mV when being applied between the two carbon electrodes for 2 seconds thereafter. Therefore, current values after the lapse of 5 seconds are recorded with respect to the respective samples.

A blood glucose measurement formula is made based on the sample having a hematocrit value of 42%. The blood glucose measurement formula is as follows.

Glucose=slope*$i_{t=5s}$(a current value after the lapse of 5 seconds)+intercept A blood glucose calibration equation is determined by calculating a slope and an intercept from the experimental data by the least squares method.

Figure 6:
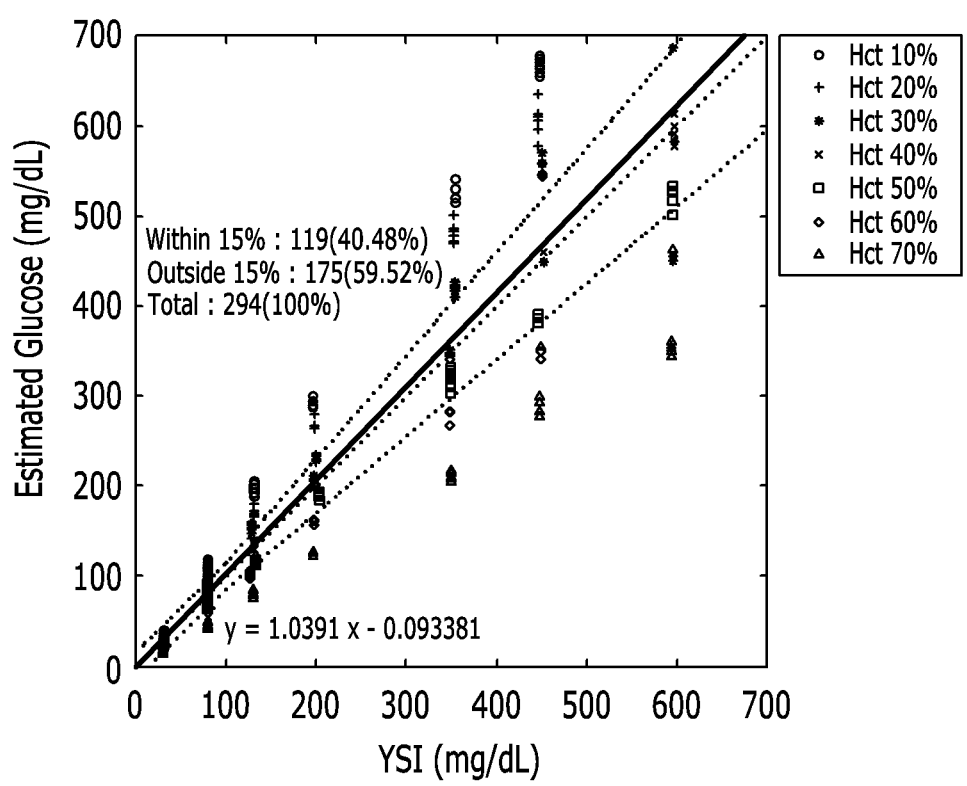
FIG. 6 is a graph illustrating a correlation between a blood glucose measurement value measured by a measuring apparatus according to chronoamperometry and a YSI measurement value in a method for measuring a concentration of an analyte in a bio-sample according to a first exemplary embodiment of the present invention.
Figure 7:
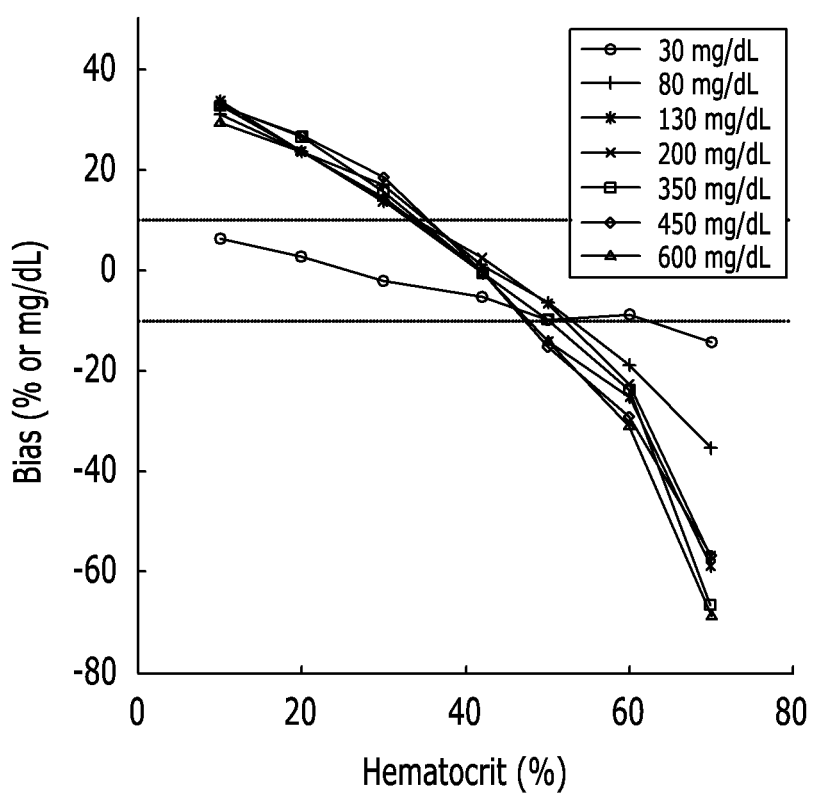
FIG. 7 is a graph illustrating an effect of hematocrit on an average value of blood glucose measurement values measured by a measuring apparatus according to chronoamperometry in the method for measuring a concentration of an analyte in a bio-sample according to the first exemplary embodiment of the present invention (a concentration of less than 100 mg/dL is expressed by an absolute error and a concentration of 100 mg/dL or more is expressed by a relative error (%)).

The results of calculation with respect to all hematocrit samples using the calibration equation obtained as such are as illustrated in FIG. 6 and FIG. 7.

FIG. 6 is a graph illustrating a correlation between a blood glucose measurement value measured by a measuring apparatus according to chronoamperometry and a YSI measurement value in a method for measuring a concentration of an analyte in a bio-sample according to a first exemplary embodiment of the present invention, and FIG. 7 is a graph illustrating an effect of hematocrit on an average value of blood glucose measurement values measured by a measuring apparatus according to chronoamperometry in the method for measuring a concentration of an analyte in a bio-sample according to the first exemplary embodiment of the present invention (a concentration of less than 100 mg/dL is expressed by an absolute error and a concentration of 100 mg/dL or more is expressed by a relative error (%)).

As illustrated in FIG. 6 and FIG. 7, in the method for measuring a concentration of an analyte in a bio-sample according to the first exemplary embodiment of the present invention, the average value of blood glucose measurement values measured by the measuring apparatus according to chronoamperometry maintains linearity with all hematocrit values. However, it can be confirmed that as hematocrit increases, a slope decreases.

Particularly, as illustrated in FIG. 7, it can be seen that, for a tendency of the blood glucose measurement values with respect to the respective hematocrit values, a deviation increases toward both ends based on 42%.

[Second Exemplary Embodiment] Example of Calibration Equation Using Features Extracted from Characteristic Points after Application of Constant Voltage and Perturbation Potential With the strip 10 and the measuring apparatus 100 used for the method for measuring a concentration of an analyte in a bio-sample according to the first exemplary embodiment of the present invention, a calibration equation minimized in effect of hematocrit can be obtained.

The experimental environment and samples used for a method for measuring a concentration of an analyte in a bio-sample according to a second exemplary embodiment of the present invention are the same as those of the first exemplary embodiment of the present invention.

A concentration measuring apparatus 100 for measuring a concentration of an analyte in a bio-sample according to a second exemplary embodiment of the present invention is different from the blood glucose measuring apparatus 100 according to the first exemplary embodiment in application of a voltage.

In the concentration measuring apparatus 100 for measuring a concentration of an analyte in a bio-sample according to a second exemplary embodiment of the present invention, firmware of the measuring apparatus 100 is modified as follows such that an appropriate perturbation potential can be applied right after a conventional constant voltage is applied.

The firmware of the concentration measuring apparatus 100 for measuring a concentration of an analyte in a bio-sample according to a second exemplary embodiment of the present invention stores a predetermined constant which can generate a perturbation potential in a memory of the measuring apparatus 100, records a predetermined constant at a register of the DAC circuit when a constant voltage is applied, and increases/decreases the constant stored in the memory at a predetermined time interval and records the constant at the register of the DAC circuit when the perturbation potential is applied.

An adequate voltage is applied between the two electrodes of the strip depending on a constant recorded at the register of the DAC circuit.

A structure of a step ladder-type perturbation potential applied as such is described in the following Table 2.

TABLE 2

| | |
|---|---|
| $V_{step}$ | 2.0 mV |
| $t_{step}$ | 0.0025 s |
| $V_{DC}$ | 200 mV |
| $V_{center}$ | 200 mV |
| $V_{peak}$ | 20 mV |
| $t_{cycle}$ | 0.1 s |

The prepared samples are measured by the blood glucose measuring apparatus 100 prepared as such. Induced currents obtained from the measurement are stored in a computer.

Features are formed of optimum characteristic points extracted by analyzing the stored data by a blood glucose formula, and a calibration equation formed of these features is formed. Then, a coefficient of each feature is determined through multivariable regression analysis so as to complete the calibration equation. The calibration equation is as follows.

$$\text{glucose} = \sum_j c_j f_j(i, T)$$

Herein, i denotes one or more current values which can be obtained from the first induced current and the second induced current, and the features used herein are as follows.

$f_1$=i at 5 s (an induced current corresponding to a constant voltage)

$f_2$=i at 5.4925 s (an induced current at a point of an ascending step of the sixth step ladder type potential)

$f_3$=i at 5.4425 s (an induced current at a point of a descending step of the fifth step ladder type potential)

$f_4$=curvature (the curvature formed of induced currents at descending steps of the fifth step ladder potential)

$f_5 = f_1^2$ $f_6 = f_2^2$ $f_7 = f_3^2$ $f_8 = f_4^2$ $f_9 = 1/f_1$
$f_{10} = 1/f_2$
$f_{11} = 1/f_3$
$f_{12} = 1/f_4$

A model formed of the above-described features is established, and in order to match blood glucose values calculated with respect to the respective samples with values measured by the YSI under various hematocrit conditions, the measuring apparatus used in the first exemplary embodiment adds a weighted value with respect to the standard hematocrit of 42% so as to be close to a concentration obtained according to chronoamperometry only, and optimizes the coefficients of the respective features by multivariable regression analysis. A new calibration equation obtained as such can minimize an effect of a hindering material while maintaining the conventional calibration method according to chronoamperometry.

The calibration equation is stored in the measuring apparatus together with firmware modified so as to apply a perturbation potential after application of a constant voltage. The results according to the new calibration equation are as illustrated in FIG. 8 and FIG. 9.

Figure 8:
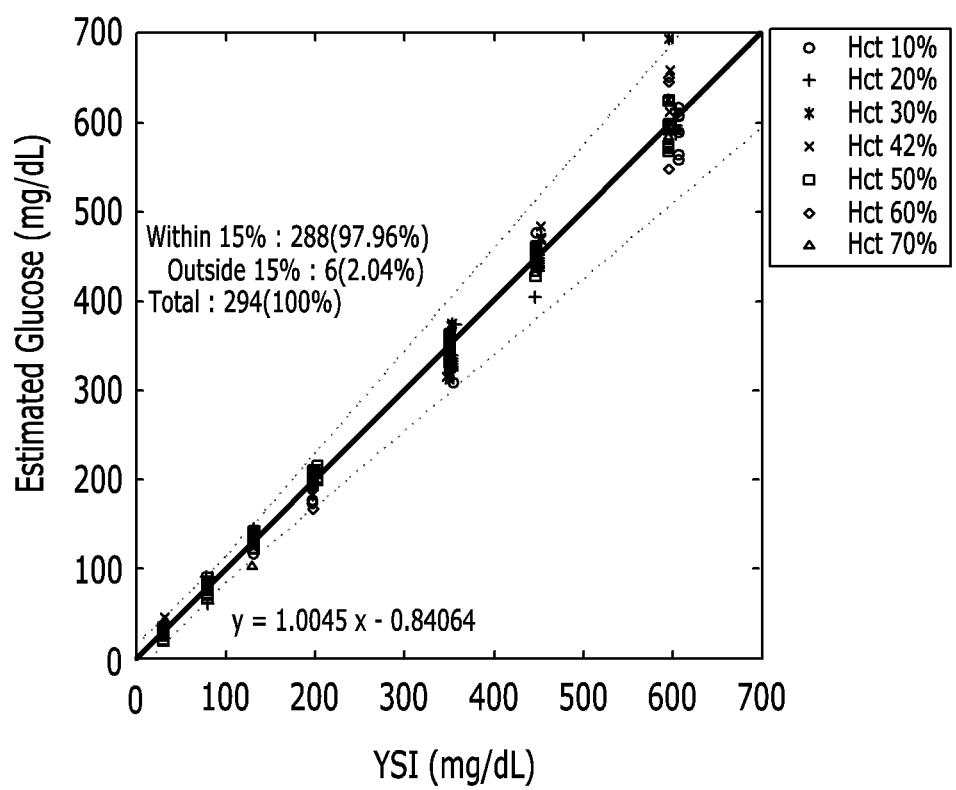
FIG. 8 is a graph illustrating a correlation between a blood glucose measurement value obtained by using chronoamperometry and a step ladder-type perturbation potential and an YSI measurement value in a method for measuring a concentration of an analyte in a bio-sample according to a second exemplary embodiment of the present invention.
Figure 9:
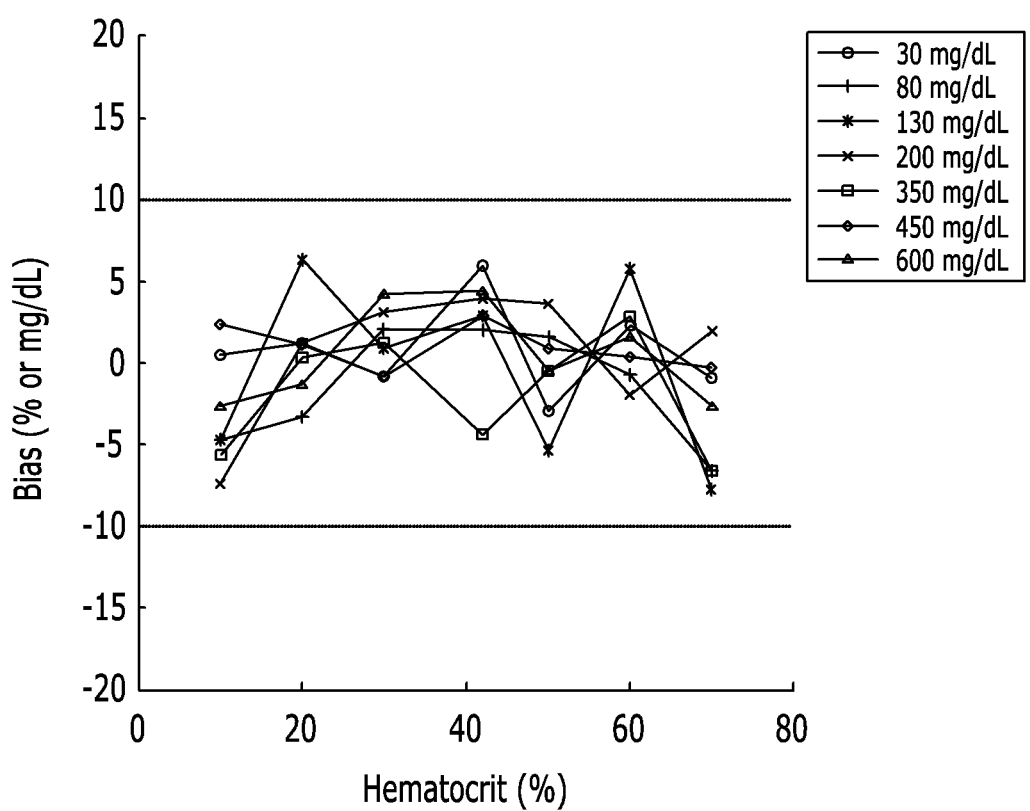
FIG. 9 is a graph illustrating an effect of hematocrit on an average value of blood glucose measurement values obtained by using chronoamperometry and a step ladder-type perturbation potential in the method for measuring a concentration of an analyte in a bio-sample according to the second exemplary embodiment of the present invention (a concentration of less than 100 mg/dL is expressed by an absolute error and a concentration of 100 mg/dL or more is expressed by a relative error (%)).

FIG. 8 is a graph illustrating a correlation between a blood glucose measurement value obtained by using chronoamperometry and a step ladder-type perturbation potential and a YSI measurement value in the method for measuring a concentration of an analyte in a bio-sample according to the second exemplary embodiment of the present invention, and FIG. 9 is a graph illustrating an effect of hematocrit on an average value of blood glucose measurement values obtained by using chronoamperometry and a step ladder-type perturbation potential in the method for measuring a concentration of an analyte in a bio-sample according to the second exemplary embodiment of the present invention (a concentration of less than 100 mg/dL is expressed by an absolute error and a concentration of 100 mg/dL or more is expressed by a relative error (%)).

As can be seen from FIG. 8, the blood glucose measurement value obtained by using chronoamperometry and a step ladder-type perturbation potential and the YSI measurement value have a very close correlation, and as can be seen from FIG. 9, the effect of hematocrit on the average value of blood glucose measurement values obtained by using chronoamperometry and a step ladder-type perturbation potential decreases to less than about ±5%.

A method for measuring a concentration of an analyte in a bio-sample according to an exemplary embodiment of the present invention will be explained with reference to FIG. 10.

Figure 10:
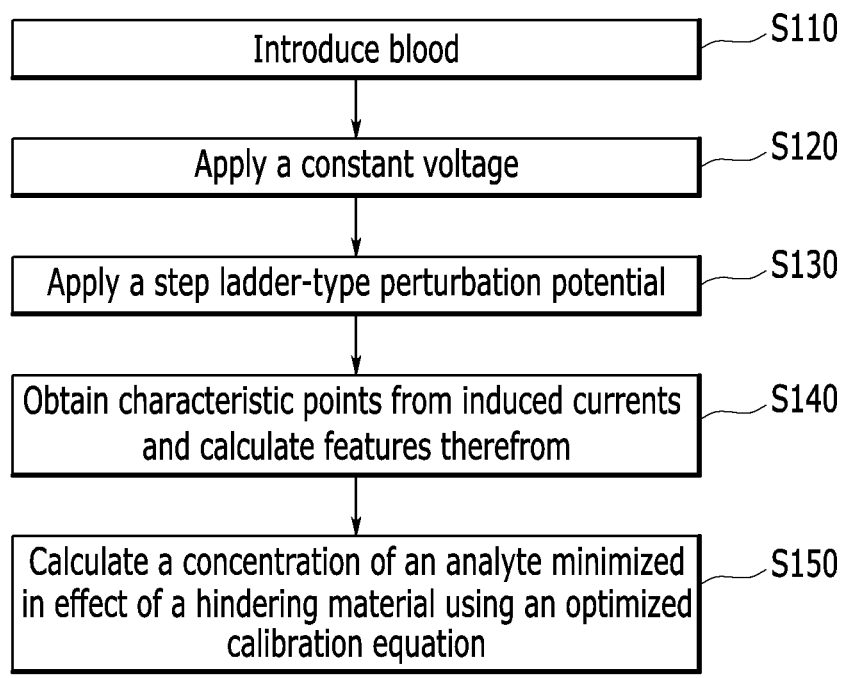
FIG. 10 is a flowchart illustrating a method for measuring a concentration of an analyte in a bio-sample according to an exemplary embodiment of the present invention.

FIG. 10 is a flowchart illustrating a method for measuring a concentration of an analyte in a bio-sample according to an exemplary embodiment of the present invention.

As illustrated in FIG. 10, a method for measuring a concentration of an analyte in a bio-sample according to an exemplary embodiment of the present invention includes a step S110 of introducing a liquid bio-sample into a sample cell in which an oxidation/reduction enzyme capable of catalyzing an oxidation/reduction reaction of the analyte and an electron transfer mediator are fixed and a working electrode and an counter electrode are provided, a step S120 of obtaining a first induced current by applying a constant DC voltage to the working electrode to start the oxidation/reduction reaction of the analyte and proceed with an electron transfer reaction, a step S130 of obtaining a second induced current by applying a Λ-step ladder-type perturbation potential after applying the constant DC voltage, a step S140 of calculating a predetermined feature from two or more characteristic points from the first induced current or the second induced current, and a step S150 of calculating a concentration of the analyte using a calibration equation formed of at least one feature function so as to minimize an effect of at least two hindering materials in the bio-sample.

After the constant DC voltage is applied, the Λ-step ladder-type perturbation potential is applied in the form of a step form wave by using a conventional DAC circuit as described above.

The step S140 of calculating a predetermined feature from the first induced current or the second induced current includes obtaining a feature from a current value at a predetermined characteristic point of the first induced current or the second induced current or by modifying the current value.

[Third Exemplary Embodiment] Example of Calibration Equation for Calculating Accurate Blood Glucose Value in Various Temperature Ranges Using Temperature as Additional Feature With the strip and the measuring apparatus used for the method for measuring a concentration of an analyte in a bio-sample according to the second exemplary embodiment of the present invention, a calibration equation minimized in effect of a temperature and hematocrit can be obtained.

The experimental environment and samples used herein are similar to those used for the method for measuring a concentration of an analyte in a bio-sample according to the second exemplary embodiment of the present invention.

That is, samples respectively having a hematocrit value of 10, 20, 42, 55, and 70% and a blood glucose concentration of 50, 130, 250, 400, and 600 mg/dL were prepared, and experiments were respectively conducted at 5, 12, 18, 23, 33, and 43° C.

A measuring apparatus 100 used for a method for measuring a concentration of an analyte in a bio-sample according to the third exemplary embodiment of the present invention is modified from the blood glucose measuring apparatus used in the second exemplary embodiment in application of a voltage.

A structure of a step ladder-type perturbation potential used for the method for measuring a concentration of an analyte in a bio-sample according to the third exemplary embodiment of the present invention is described in the following Table 3.

TABLE 3

| | |
|---|---|
| $V_{step}$ | 2.0 mV |
| $t_{step}$ | 0.005 s |
| $V_{DC}$ | 200 mV |
| $V_{center}$ | 200 mV |
| $V_{peak}$ | 20 mV |
| $t_{cycle}$ | 0.2 s |

The prepared samples are measured at each temperature by the measuring apparatus 100 prepared as such. Induced currents obtained from the measurement are stored in a computer.

Features are formed of optimum characteristic points extracted by analyzing the stored data by a blood glucose formula, and a calibration equation formed of these features is formed. Then, a coefficient of each feature is determined through multivariable regression analysis so as to complete the calibration equation. The calibration equation is as follows.

$$\text{ketone body} = \sum_j c_j f_j(i)$$

Herein, i denotes one or more current values which can be obtained from the first induced current and the second induced current, T denotes temperature values that are independently measured, and the features used herein are as follows.

$f_1$=i at 5 s (an induced current corresponding to a constant voltage)

$f_2$=i at 5.2675 s (an induced current at a point descending from a peak of the second step ladder type potential)

$f_3$=i at 5.3675 s (an induced current at a point ascending from a valley of the third step ladder type potential)

$f_4$=curvature (the curvature formed of induced currents at descending steps of the second step ladder potential)

$f_5$=Peak-to-Peak (a difference between a peak voltage and a valley voltage of the second step ladder potential)

$f_6 = f_1^2$
$f_7 = f_2^2$
$f_8 = f_3^2$
$f_9 = f_4^2$
$f_{10} = f_5^2$
$f_{11} = 1/f_1$
$f_{12} = 1/f_4$
$f_{13} = T$
$f_{14} = T^2$
$f_{15} = f_1 * T$

A model formed of the above-described features is established, and as explained in the second exemplary embodiment of the present invention, the coefficients of the respective features are optimized by multivariable regression analysis based on the blood glucose values measured by the reference equipment YSI.

A calibration equation obtained as such is stored in the measuring apparatus together with firmware modified so as to apply a perturbation potential after application of a constant voltage in the same manner as the second exemplary embodiment. The results according to the new calibration equation are as illustrated in FIG. 11 and FIG. 12.

Figure 11:
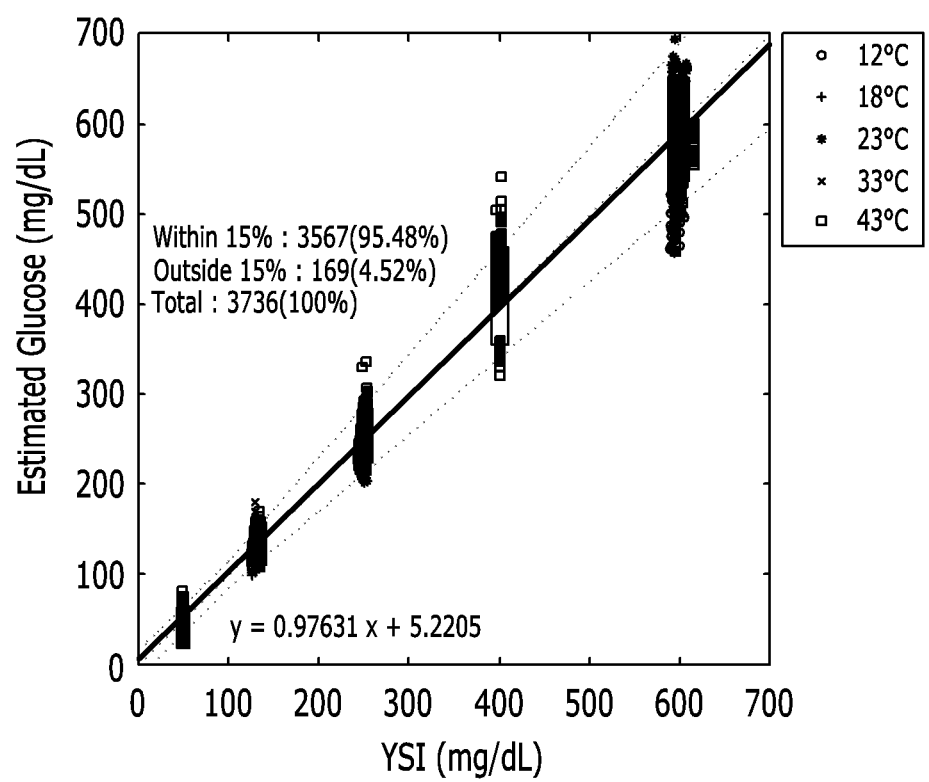
FIG. 11 is a graph illustrating a correlation between a blood glucose measurement value obtained by using chronoamperometry, a step ladder-type perturbation potential, and a temperature value measured by a measuring apparatus and a YSI measurement value in a method for measuring a concentration of an analyte in a bio-sample according to a third exemplary embodiment of the present invention (including samples respectively having a hematocrit value of 10, 20, 42, 55, and 70%).

FIG. 11 is a graph illustrating a correlation between a blood glucose measurement value obtained by using chronoamperometry, a step ladder-type perturbation potential, and a temperature value measured by a measuring apparatus and a YSI measurement value in the method for measuring a concentration of an analyte in a bio-sample according to the third exemplary embodiment of the present invention (including samples respectively having a hematocrit value of 10, 20, 42, 55, and 70%).

Figure 12:
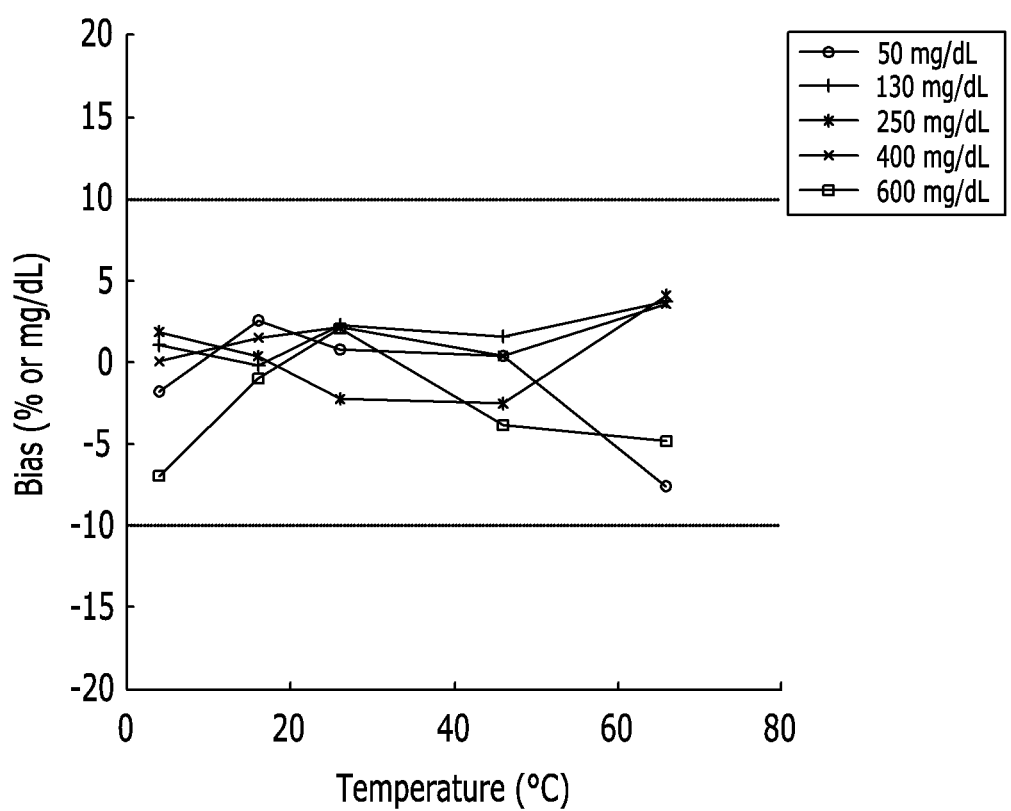
FIG. 12 is a graph illustrating an effect of temperature on an average value of blood glucose measurement values obtained by using chronoamperometry, a step ladder-type perturbation potential, and a temperature value measured by a measuring apparatus in the method for measuring a concentration of an analyte in a bio-sample according to the third exemplary embodiment of the present invention (including samples having a hematocrit value of 10, 20, 42, 55, and 70%; a concentration of less than 100 mg/dL is expressed by an absolute error and a concentration of 100 mg/dL or more is expressed by a relative error (%)).

FIG. 12 is a graph illustrating an effect of temperature on an average value of blood glucose measurement values obtained by using chronoamperometry, a step ladder-type perturbation potential, and a temperature value measured by a measuring apparatus in the method for measuring a concentration of an analyte in a bio-sample according to the third exemplary embodiment of the present invention (a concentration of less than 100 mg/dL is expressed by an absolute error and a concentration of 100 mg/dL or more is expressed by a relative error (%)).

As illustrated in FIG. 10, measurement of a blood glucose value includes introducing blood, applying a constant voltage, applying a step ladder-type perturbation potential, calculating features from induced currents, and obtaining an accurate blood glucose value using the new calibration equation.

[Fourth Exemplary Embodiment] Example of Calibration Equation for Measuring Ketone Body In a method for measuring a concentration of an analyte in a bio-sample according to a fourth exemplary embodiment of the present invention, a sample cell of the electrochemical bio-sensor 10 is a disposable strip formed of two screen-printed carbon electrodes, and if the electrodes are coated with a ketone body dehydrogenase and an electron transfer mediator (1-methoxy-5-methylphenazinium methyl sulfate, ruthenium hexamine chloride), an induced current is obtained by applying a constant voltage at 23° C. and a ketone body concentration is calculated.

Blood experiments for checking a deviation caused by hematocrit are conducted similarly to the first exemplary embodiment. Blood samples respectively having a hematocrit value of 20, 30, 42, 50, 60, and 70% are prepared.

The blood samples are prepared such that ketone body concentrations can be approximately 0.1, 0.5, 1, 2, 3, 4.2, and 5 mmol/L with respect to the respective hematocrit values, and an actual blood glucose value of each sample is measured by reference equipment (RX Monaco, Randox) and then determined.

Meanwhile, the measuring apparatus having the same structure as the blood glucose measuring apparatus used in the above-described exemplary embodiment records an induced current corresponding to a constant voltage.

An applied voltage used herein is 200 mV when being applied between the two electrodes within the strip for 4 seconds after inflow of blood, is 0 mV when being applied for 4 seconds thereafter, and then is 200 mV when being applied for 2 seconds thereafter.

Current values after the lapse of 10 seconds are recorded with respect to the respective samples.

A ketone body measurement formula is made based on the sample having a hematocrit of 42%.

The ketone body measurement formula is as follows.

Ketone Body=slope*$i_{t=10s}$(a current value after the lapse of 10 seconds)+intercept A calibration equation is obtained by calculating a slope and an intercept from the experimental data by the least square method experimental data.

Figure 13:
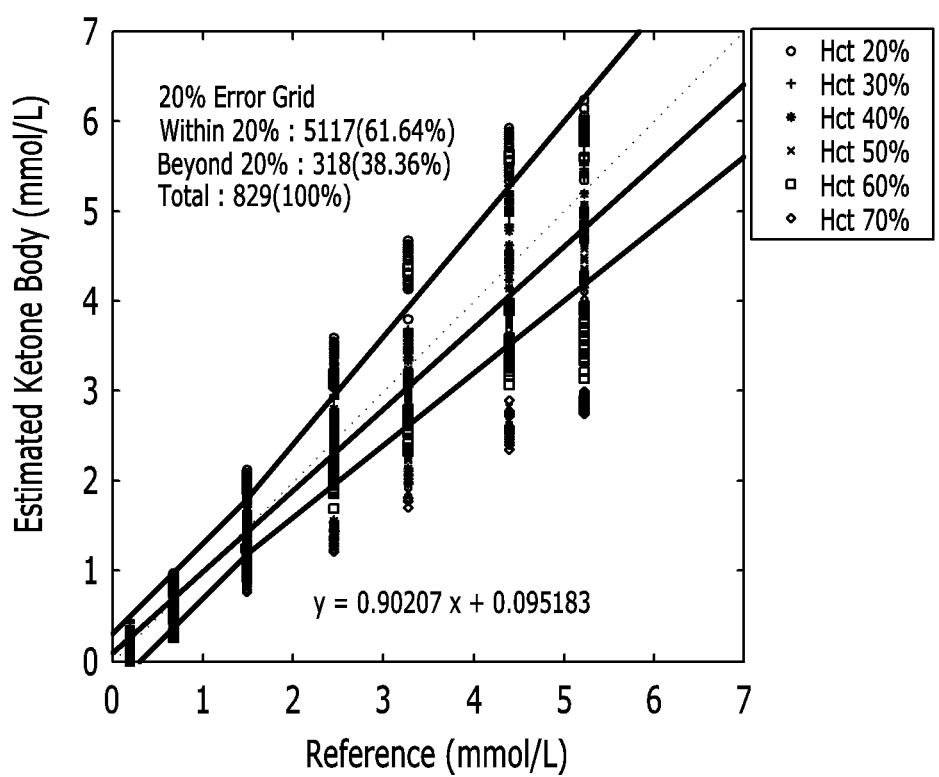
FIG. 13 is a graph illustrating a correlation between a ketone body measurement value obtained according to chronoamperometry and a measurement value measured by reference equipment in a method for measuring a concentration of an analyte in a bio-sample according to a fourth exemplary embodiment of the present invention.
Figure 14:
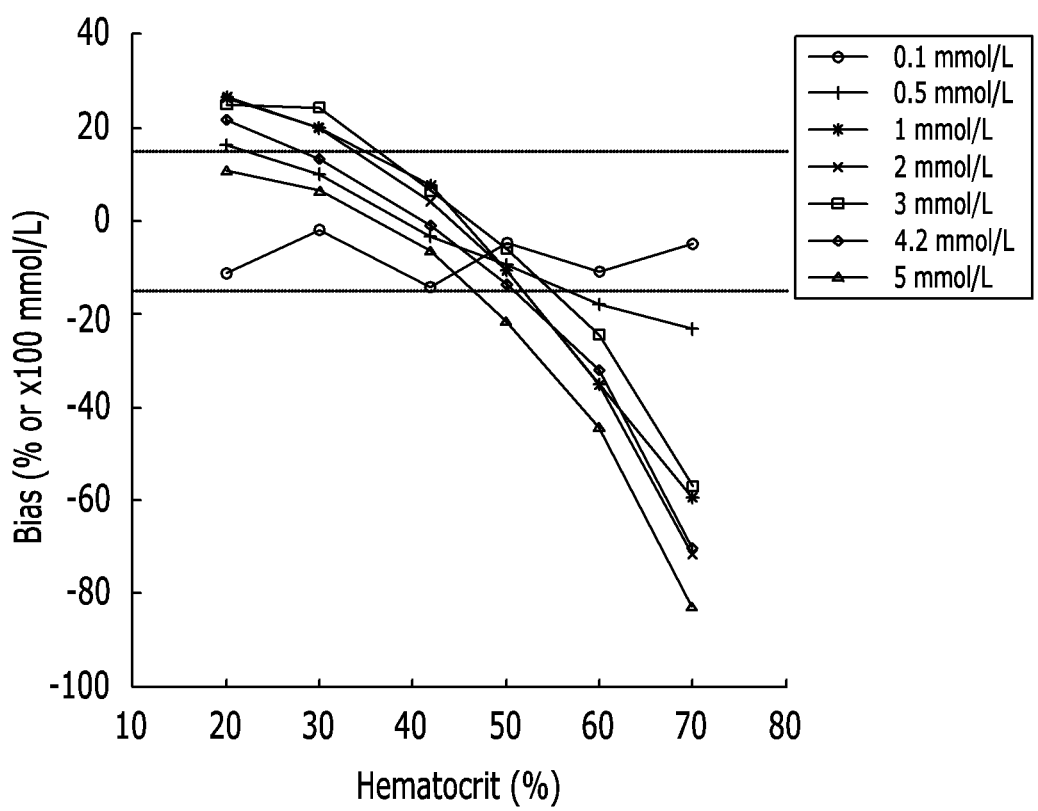
FIG. 14 is a graph illustrating an effect of hematocrit on an average value of ketone body measurement values obtained according to chronoamperometry in the method for measuring a concentration of an analyte in a bio-sample according to the fourth exemplary embodiment of the present invention (a concentration of less than 1.0 mmol/L is expressed by an absolute error multiplied by 100 and a concentration of 1.0 mmol/L or more is expressed by a relative error (%)).

The results of calculation with respect to all hematocrit samples using the ketone body calibration equation obtained as such are as illustrated in FIG. 13 and FIG. 14.

FIG. 13 is a graph illustrating a correlation between a ketone body measurement value obtained according to chronoamperometry and a measurement value measured by reference equipment in the method for measuring a concentration of an analyte in a bio-sample according to the fourth exemplary embodiment of the present invention, and FIG. 14 is a graph illustrating an effect of hematocrit on an average value of ketone body measurement values obtained according to chronoamperometry in the method for measuring a concentration of an analyte in a bio-sample according to the fourth exemplary embodiment of the present invention (a concentration of less than 1.0 mmol/L is expressed by an absolute error multiplied by 100 and a concentration of 1.0 mmol/L or more is expressed by a relative error (%)).

As illustrated in FIG. 13 and FIG. 14, it can be confirmed that the average value of ketone body measurement values obtained according to chronoamperometry has a decreasing slope as hematocrit increases.

Further, as illustrated in FIG. 14, it can be seen that, for a tendency of the ketone body measurement values with respect to the respective hematocrit values according to chronoamperometry, a deviation increases toward both ends based on 42%.

[Fifth Exemplary Embodiment] Example of Calibration Equation for Measuring Ketone Body Using Features Extracted from Characteristic Points after Application of Constant Voltage and Perturbation Potential With the strip and the measuring apparatus used for the method for measuring a concentration of an analyte in a bio-sample according to the fourth exemplary embodiment of the present invention, a calibration equation for measuring a ketone body using features extracted from characteristic points after application of a constant voltage and a perturbation potential can be obtained.

The experimental environment and samples used herein are the same as those used for the method for measuring a concentration of an analyte in a bio-sample according to the fourth exemplary embodiment of the present invention.

A measuring apparatus is different from the measuring apparatus used in the fourth exemplary embodiment in application of a voltage. That is, firmware of the measuring apparatus is modified such that a perturbation potential described in the following table can be applied right after a conventional constant voltage is applied.

In a method for measuring a concentration of an analyte in a bio-sample according to the fifth exemplary embodiment of the present invention, a voltage is applied in the form of a step ladder-type perturbation potential described in the following Table 4 right after the voltage used in the fourth exemplary embodiment.

TABLE 4

| | |
|---|---|
| $V_{step}$ | 1.5 mV |
| $t_{step}$ | 0.0025 s |
| $V_{DC}$ | 200 mV |
| $V_{center}$ | 250 mV |
| $V_{peak}$ | 15 mV |
| $t_{cycle}$ | 0.1 s |

The prepared samples are measured by the measuring apparatus prepared as such. Induced currents obtained from the measurement are stored in a computer.

Features are formed of optimum characteristic points extracted by analyzing the stored data by a blood glucose formula, and a calibration equation formed of these features is formed. Then, a coefficient of each feature is determined through multivariable regression analysis so as to complete the calibration equation.

The calibration equation for measuring a ketone body is as follows.

$$\text{ketone body} = \sum_j c_j f_j(i)$$

Herein, i denotes one or more current values which can be obtained from the first induced current and the second induced current, and the features used herein are as follows.

$f_1$=current at 10 s (an induced current corresponding to a constant voltage)

$f_2$=current at 8.12 s (an initial induced current corresponding to a constant voltage)

$f_3$=current at 10.27 s (an induced current at a voltage near a valley of the third step ladder type potential)

$f_4$=current at 10.4925 s (an induced current at a voltage near a valley of the fifth step ladder type potential)

$f_5$=curvature (the curvature formed of induced currents at descending steps of the fifth step ladder potential)

$f_6 = f_1^2$
$f_7 = f_2^2$
$f_8 = f_3^2$
$f_9 = f_4^2$
$f_{10} = f_5^2$
$f_{11} = 1/f_1$
$f_{12} = 1/f_5$

A model formed of the above-described features is established, and in order to match blood glucose values calculated with respect to the respective samples with values measured by the reference equipment under various hematocrit conditions, a weighted value is added with respect to the standard hematocrit of 42% so as to be close to a concentration obtained according to chronoamperometry only, and the coefficients of the respective features are optimized by multivariable regression analysis.

A calibration equation obtained as such is stored in the measuring apparatus together with firmware modified so as to apply a perturbation potential after application of a constant voltage. The results according to the calibration equation are as illustrated in FIG. 15 and FIG. 16.

Figure 15:
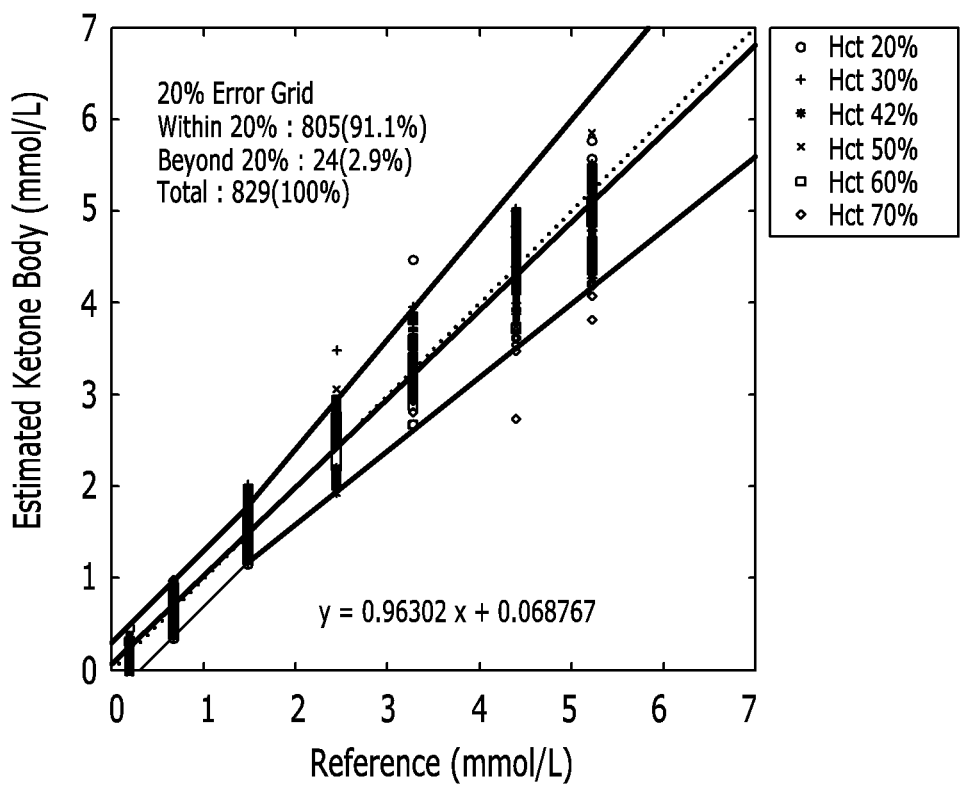
FIG. 15 is a graph illustrating a correlation between a ketone body measurement value obtained by using chronoamperometry and a step ladder-type perturbation potential and a measurement value measured by a reference equipment in a method for measuring a concentration of an analyte in a bio-sample according to a fifth exemplary embodiment of the present invention.
Figure 16:
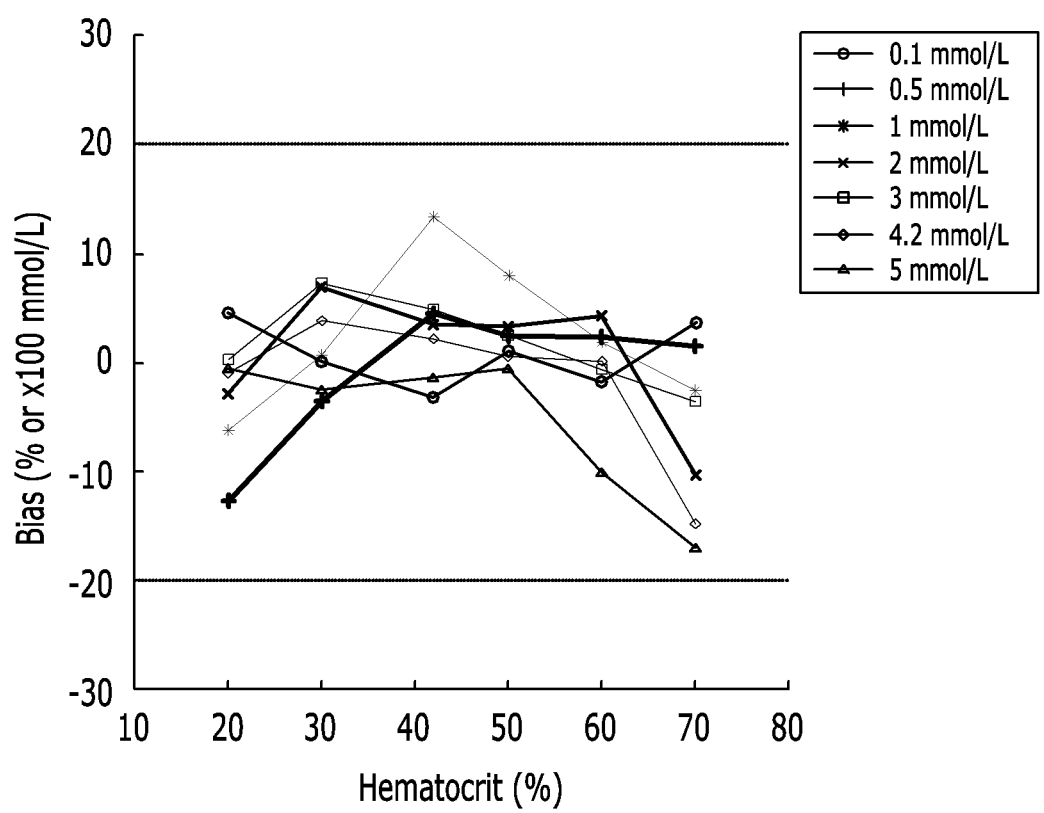
FIG. 16 is a graph illustrating an effect of hematocrit on an average value of ketone body measurement values obtained by using chronoamperometry and a step ladder-type perturbation potential in the method for measuring a concentration of an analyte in a bio-sample according to the fifth exemplary embodiment of the present invention (a concentration of less than 1.0 mmol/L is expressed by an absolute error multiplied by 100 and a concentration of 1.0 mmol/L or more is expressed by a relative error (%)).

FIG. 15 is a graph illustrating a correlation between a ketone body measurement value obtained by using chronoamperometry and a step ladder-type perturbation potential and a measurement value measured by a reference equipment in the method for measuring a concentration of an analyte in a bio-sample according to the fifth exemplary embodiment of the present invention, and FIG. 16 is a graph illustrating an effect of hematocrit on an average value of ketone body measurement values obtained by using chronoamperometry and a step ladder-type perturbation potential in the method for measuring a concentration of an analyte in a bio-sample according to the fifth exemplary embodiment of the present invention (a concentration of less than 1.0 mmol/L is expressed by an absolute error multiplied by 100 and a concentration of 1.0 mmol/L or more is expressed by a relative error (%)).

The effect of the method for measuring a concentration of an analyte in a bio-sample according to the exemplary embodiments of the present invention can be clearly seen by comparing the first exemplary embodiment with the second exemplary embodiment of the present invention and comparing the third exemplary embodiment with the fourth exemplary embodiment.

That is, it is possible to directly obtain a result that is minimized in matrix effect of a hindering factor such as hematocrit from calibration equation, without using an additional correction formula, by using a conventional biosensor in a measuring apparatus according to the generally-used chronoamperometry and adding a step ladder-type perturbation potential (FIG. 1) to a conventional voltage application method only for a short time.

Further, as can be seen from the third exemplary embodiment of the present invention, if a calibration equation is obtained using a temperature measured by a measuring apparatus as an additional feature, it is possible to obtain a measurement result that is minimized in both of a matrix effect and a temperature effect by a simple calculation.

While this invention has been described in connection with what is presently considered to be practical exemplary embodiments, it is to be understood that the invention is not

| <Description of symbols> | |
|---|---|
| 10: Electrochemical bio-sensor (Strip) | 100: Measuring apparatus |
| 110: Connector | 120: Current-voltage converter |
| 130: DAC circuit | 140: ADC circuit |
| 150: Microcontroller | |

What is claimed is:

1. A method for measuring a concentration of an analyte in a bio-sample, the method comprising:
a step of introducing a liquid bio-sample into a sample cell in which an oxidation/reduction enzyme capable of catalyzing an oxidation/reduction reaction of the analyte and an electron transfer mediator are fixed and a working electrode and a counter electrode are provided;
a step of obtaining a first induced current by applying a constant DC voltage to the working electrode to start the oxidation/reduction reaction of the analyte and proceed with an electron transfer reaction;
a step of obtaining a second induced current by applying a Λ-step ladder-type perturbation potential after applying the constant DC voltage, wherein the step of obtaining the second induced current is subsequent to the step of obtaining the first induced current;
a step of calculating a predetermined feature from two or more characteristic points from the first induced current or the second induced current; and
a step of calculating a concentration of the analyte using a calibration equation formed of at least one feature function so as to minimize an effect of at least one hindering material in the bio-sample, wherein the at least one feature function comprises a function using the first induced current obtained from the constant DC voltage and a function using the second induced current obtained from the Λ-step ladder-type perturbation potential,
wherein the Λ-step ladder-type perturbation potential is characterized by a height ($V_{step}$) of each step, an application time ($t_{step}$) for each step, a difference ($V_{center}$) between a middle voltage and the constant DC voltage in an entire range of variations, a difference ($V_{peak}$) between a middle voltage and a peak voltage, and a time difference ($t_{cycle}$) between a peak voltage of an entire step ladder-type wave and a peak voltage of an adjacent next step ladder-type wave,
wherein the constant DC voltage and the Λ-step ladder-type perturbation potential are applied to the working electrode through a same digital-to-analog converter circuit linked with a microcontroller, and
wherein a characteristic point, having different linearity with respect to the analyte and the hindering material, is selected from the first or second induced current, wherein a feature is formed of the characteristic point, and wherein a calibration equation is formed of the feature.

2. The method for measuring a concentration of an analyte in a bio-sample of claim 1, wherein
the second induced current is obtained within 0.1 to 1 second after the first induced current is obtained.

3. The method for measuring a concentration of an analyte in a bio-sample of claim 1, wherein
the feature is formed of the characteristic point by using one of second induced currents near peak and valley voltages of a specific step ladder type, curvature of a curved line formed of induced currents of each step of the Λ-step ladder-type perturbation potential, a difference between a current value of a peak and a current value of a valley of the Λ-step ladder-type perturbation potential, induced currents in the middle of ups and downs of the Λ-step ladder-type perturbation potential, induced currents at a starting point and an ending point of each step ladder-type perturbation potential cycle, and an average value of induced currents obtained from the Λ-step ladder-type perturbation potential, and values which can be obtained by expressing the current values obtained therefrom by four fundamental arithmetic operations and mathematical functions including an exponential function, a logarithmic function, and a trigonometric function are used.

4. The method for measuring a concentration of an analyte in a bio-sample of claim 1, wherein
the calibration equation formed of at least one feature function is obtained by applying multivariable regression analysis to the at least one feature function as a linear mixture of the at least one feature function, and the calibration equation varies depending on a material of the working and counter electrodes, an arrangement of the working and counter electrodes, a shape of a flow path, and a characteristic of a reagent to be used.

5. The method for measuring a concentration of an analyte in a bio-sample of claim 4, wherein
the analyte is one of glucose, β-hydroxybutyric acid, cholesterol, triglyceride, lactate, pyruvate, alcohol, bilirubin, uric acid, phenylketonuria, creatine, creatinine, glucose-6-phosphate dehydrogenase, NAD(P)H, and a ketone body.

6. The method for measuring a concentration of an analyte in a bio-sample of claim 4, wherein
the oxidation/reduction enzyme is one of a glucose oxidase (GOx), a glucose dehydrogenase (GDH), a glutamate oxidase, a glutamate dehydrogenase, a cholesterol oxidase, a cholesterol esterase, a lactate oxidase, an ascorbic acid oxidase, an alcohol oxidase, an alcohol dehydrogenase, a bilirubin oxidase, and a ketone body dehydrogenase.

7. The method for measuring a concentration of an analyte in a bio-sample of claim 1, wherein
the electron transfer mediator which can be used together with the oxidation/reduction enzyme is one of ferrocene, ruthenium hexamine(III) chloride, potassium ferricyanide, 1,10-phenanthroline-5,6-dione, and bipyridine, or an osmium complex including phenanthroline as a ligand, 2,6-dimethyl-1,4-benzoquinone, 2,5-dichloro-1,4-benzoquinone, 3,7-diamino-5-phenothiaziniumthionine, 1-methoxy-5-methylphenazinium methylsulfate, methylene blue, and toluidine blue.

8. The method for measuring a concentration of an analyte in a bio-sample of claim 1, wherein
the constant DC voltage having a voltage range of 0 to 800 mV is consecutively or intermittently applied for 1 second or more to less than 1 minute, and the first induced current is measured one time or several times while the constant DC voltage is applied.

9. The method for measuring a concentration of an analyte in a bio-sample of claim 1, wherein
a height ($V_{step}$) of a step of the Λ-step ladder-type potential is 0.5 to 20 mV, a duration time ($t_{step}$) of the step is 0.001 to 0.1 second, a difference ($V_{center}$)

between a middle voltage and a constant voltage of the step Λ step ladder-type potential is −150 to 150 mV, a difference ($V_{peak}$) between the middle voltage and a peak or valley voltage of the Λ-step ladder-type potential is 5 to 150 mV, and a cycle of the Λ-step ladder-type potential or a time difference ($t_{cycle}$) between a peak and an adjacent next peak is in a range of 0.01 to 1 second.

10. The method for measuring a concentration of an analyte in a bio-sample of claim 1, wherein:

the at least one feature function further comprises a function using a temperature value measured by a measuring apparatus, and a function which can be obtained by expressing measured current values by four fundamental arithmetic operations and mathematical functions including an exponential function, a logarithmic function, and a trigonometric function.

11. The method for measuring a concentration of an analyte in a bio-sample of claim 1, wherein the calibration equation formed of at least one feature function is one of glucose=$E_j \Box c_j f_j(i)$,
glucose=$E_j \Box c_j f_j(i,T)$, and
ketone body=$E_j \Box c_j f_j(i)$, wherein i denotes one or more current values which can be obtained from the first induced current and the second induced current, c denotes a constant, j denotes a number, and T denotes temperature values that are independently measured.

* * * * *